(12) United States Patent
Weldele et al.

(10) Patent No.: US 7,259,185 B2
(45) Date of Patent: Aug. 21, 2007

(54) STABLE WARFARIN SODIUM LIQUID FORMULATION AND METHOD OF MAKING SAME

(75) Inventors: Meagan Erica Weldele, Overland Park, KS (US); David Delmarre, Vernon Hills, IL (US); Danchen Gao, Chicago, IL (US); Mahmoud Assad El-Khateeb, Dublin, OH (US); Carlos-Julian Sison Centeno, Chicago, IL (US); Shitalkumar Ratnakar Pathak, Mundelein, IL (US)

(73) Assignee: Morton Grove Pharmaceuticals, Inc., Morton Grove, IL (US)

( * ) Notice: Subject to any disclaimer, the term of this patent is extended or adjusted under 35 U.S.C. 154(b) by 0 days.

(21) Appl. No.: 11/453,757

(22) Filed: Jun. 14, 2006

(65) Prior Publication Data

US 2006/0293382 A1    Dec. 28, 2006

Related U.S. Application Data

(60) Provisional application No. 60/691,123, filed on Jun. 15, 2005.

(51) Int. Cl.
*A61K 31/37* (2006.01)
*C07D 311/56* (2006.01)

(52) U.S. Cl. .................. 514/457; 549/286

(58) Field of Classification Search ............ 549/286; 514/457
See application file for complete search history.

(56) References Cited

U.S. PATENT DOCUMENTS

| | | | |
|---|---|---|---|
| 2,999,049 A | 9/1961 | Link | 167/65 |
| 3,121,664 A * | 2/1964 | Hiskey et al. | 514/457 |
| 3,485,922 A | 12/1969 | Badran | 424/281 |
| 6,365,180 B1 | 4/2002 | Meyer et al. | 424/451 |
| 6,469,227 B1 | 10/2002 | Cooke et al. | 602/48 |
| 2002/0120157 A1 | 8/2002 | Michel et al. | 549/289 |
| 2004/0022862 A1 | 2/2004 | Kipp et al. | 424/490 |
| 2004/0258757 A1 | 12/2004 | Bosch et al. | 424/489 |

FOREIGN PATENT DOCUMENTS

| | | |
|---|---|---|
| SU | 1587714 | 5/1991 |
| WO | WO 85/03202 | 8/1985 |
| WO | WO2004/024126 | 3/2004 |

OTHER PUBLICATIONS

"Coumadin® Tablets; Coumadin® for Injection," XP-002409141 (Dec. 14, 2004).

* cited by examiner

*Primary Examiner*—Bernard Dentz
(74) *Attorney, Agent, or Firm*—Winston & Strawn LLP

(57) ABSTRACT

A stable liquid composition comprising warfarin sodium, glycerin, an alcohol such as ethanol, and a pH buffer such as a phosphate buffer providing a pH above 7 is provided. The stability of the composition is characterized by the amount of warfarin sodium in the composition degraded after 1 month at room temperature, which is 5% or less. A method for preparing the composition and a method for providing an anti-coagulant therapy are also disclosed.

26 Claims, 5 Drawing Sheets

STABLE WARFARIN SODIUM LIQUID FORMULATION AND METHOD OF MAKING SAME

This application claims the benefit of Provisional Application No. 60/691,123 filed Jun. 15, 2005, the entire content of which is expressly incorporated herein by reference thereto.

FIELD OF INVENTION

The present invention relates generally to preparation of a stable liquid form of warfarin sodium. In particular, the invention relates to a method of preparing stable warfarin sodium liquid formulations suitable for oral and parenteral administration and formulations produced thereby.

BACKGROUND OF THE INVENTION

Warfarin sodium, known by the chemical name 4-hydroxy-3-(3-oxo-1-phenylbutyl)-2H-1-benzopyran-2one sodium salt, has the structure represented by Formula 1:

Formula I

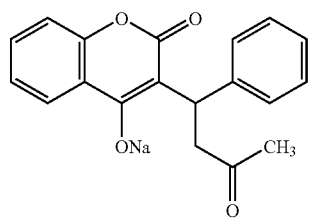

Warfarin sodium has a molecular weight of 360.37 g/mol; is known to crystallize only as a clathrate with isopropyl alcohol as the guest molecule; and is monoclinic in the crystalline form.

Warfarin sodium is a well-established, widely-used anticoagulant that acts by blocking the synthesis of vitamin K-dependent coagulation factors (II, VII, IX, and X). There are a number of related conditions for which warfarin sodium is prescribed such as venous thrombosis, pulmonary embolism, myocardial infarction, and progressive stroke. Warfarin is administered as a racemic mixture of two enantiomers which have markedly different metabolism and activity. The $t_{1/2}$ of racemic warfarin ranges from 40 to 60 hours. Oral absorption of warfarin is rapid (2-6 hours) and extensive (F≈1). Warfarin is highly bound to albumin in plasma (≈99%) and has apparent $V_d$ of 0.13 L/kg. Warfarin has a low hepatic extraction ratio and elimination occurs almost entirely by metabolism (>99%). Warfarin is known to have both pharmacokinetic and pharmacodynamic interactions with a number of drugs including barbiturates, rifampicin, cimetidine, phenylbutazone, and salicylate.

Currently, warfarin sodium for oral administration is provided only in tablet form, and no warfarin sodium product is available in oral liquid form.

Even the warfarin sodium products for intravenous injection currently available in the market are not provided in liquid form but as lyophilized powder that is reconstituted with sterile water immediately prior to injection. For example, Coumadin®, a warfarin sodium drug produced by Bristol-Myers Squibb Company, is available for intravenous injection but is provided as lyophilized powder in a vial. The powder is reconstituted with sterile water for intravenous injection, and must be used within 4 hours of reconstitution because the warfarin sodium formulation is chemically and physically stable only for 4 hours at room temperature. After reconstitution, the warfarin sodium formulation must be stored at controlled room temperature (15-30° C.), and any unused solution must be discarded.

U.S. Pat. No. 2,999,049 also discloses warfarin sodium composition for intravenous or intramuscular injection. This reference is directed to providing a intravenous or intramuscular composition containing both warfarin sodium and heparin sodium, and, while disclosing a liquid form of the composition as well as a dry lyophilized form, the reference also discloses that a solid product substantially free of moisture is preferred for overall stability during long periods of storage.

Thus, there is no currently available liquid form of warfarin sodium that can be orally administered. Further, the available injectable form of warfarin sodium presents a number of disadvantages. Not only is it difficult to administer since it requires reconstitution with water before use, but warfarin sodium currently available for intravenous injection must also be carefully monitored during administration to ensure sterility. For instance, reconstitution must be carried out under sterile conditions, the reconstituted Solution must be inspected for presence of particulate matter or discoloration, and sterility must be maintained throughout the injection procedure. In addition, administration of the existing injectable warfarin sodium solution is constrained by time because the solution must be used within 4 hours of reconstitution, and may involve additional waste since the vial containing lyophilized powder of warfarin sodium cannot be used multiple times and unused portions of reconstituted solution must be discarded.

In view of the current state of the art, a liquid form of warfarin sodium that is stable in the long term and does not require reconstitution is desired. Such stable warfarin sodium liquid would not only be safer to administer than the conventional injectable warfarin sodium, but would also be more user-friendly and easier to administer and therefore would help eliminate mistakes associated with administration of the existing warfarin sodium product.

Further, a stable warfarin sodium liquid form that can be orally administered is desired, especially since the dosage form of warfarin sodium (solution or tablet) does not seem to significantly affect plasma levels. The amount absorbed is also not affected by food, volume of fluid ingested, or dosage form. Until now, however, the difficulty of producing a stable liquid form of warfarin sodium has prevented commercialization of the drug in oral liquid form despite its potential advantages over the conventional tablet form for providing easy administration even to patients who have trouble swallowing tablets. A drinkable form of warfarin sodium is further advantageous over intravenous injection, since it is much more convenient to use and can be administered without a physician's supervision or special equipments.

Hence, what is needed is a stable liquid form of warfarin sodium that can be adapted for parenteral as well as oral administration. The present invention addresses the problems of the prior art by providing a liquid warfarin sodium formulation that is stable in the long term and can be conveniently administered.

SUMMARY OF THE INVENTION

The present invention generally relates to a stable liquid composition comprising warfarin sodium and the method of preparation.

According to one aspect of the invention, the liquid composition comprises warfarin sodium as an active ingredient, glycerin in an amount effective to act as a stabilizer in all pH ranges considered, an alcohol such as ethanol in an amount sufficient to stabilize the composition and help inhibit precipitation of warfarin at lower pHs, and a pH buffer such as a phosphate buffer providing a pH above 7 in an amount sufficient to control the pH to a desired range. The present liquid composition is stable in the long term, as characterized by the amount of warfarin sodium degraded after 1 month at room temperature being 5% or less.

In one embodiment, glycerin is present in an amount of about 1 to 93% of the composition by volume and the alcohol is present in an amount of about 0 to 20% by volume.

According to a preferred embodiment, the composition is an orally administratable or oral composition, which can be provided in any convenient or suitable form, including a solution, a syrup, a suspension, an elixir and a concentrate. The composition can comprise additional ingredients, including a chelating agent such as EDTA or TPGS, pepsin, albumin, a surfactant, a cellulose such as hydroxyproxymethyl cellulose (HPMC) or povidone (PVP), a polyethylene glycol (PEG), propylene glycol (PG), a gum, an oil, a fatty acid, a sweetener such as saccharin, sorbitol, mannitol, and liquid sugar, and an antioxidant such as vitamin E. A pH of about 5 to 9 can be provided by the pH buffer.

In one embodiment, the amount of warfarin sodium present in the composition is about 0.1 mg/mL to about 20 mg/mL. Preferably, about 1 mg/mL of warfarin sodium is included.

Further, the present composition can provide a self-antimicrobial (or preservative-free) activity in addition to the anticoagulant function provided by warfarin sodium.

The present warfarin sodium composition can be provided in any suitable container and in any dose desired for particular use. For example, the composition is provided in a container comprising high-density polyethylene (HDPE), or in a brown-colored glass container.

In another aspect, the invention relates to a method for preparing a stable liquid composition that includes warfarin sodium as an active ingredient, which comprises providing glycerin in the composition in an amount effective to act as a stabilizer, providing an alcohol in the composition an amount sufficient to stabilize the composition and help inhibit reprecipitation of warfarin, and providing the composition with a pH above 5, wherein the composition is sufficiently stable such that amount of warfarin sodium in the composition that is degraded after 6 month at room temperature is about 5% or less.

In yet another aspect, a method for providing an anticoagulant therapy is provided. Preferably, the amount of warfarin sodium administered according to the present method is about 0.1 mg/mL to about 20 mg/mL per day.

BRIEF DESCRIPTION OF THE DRAWINGS

The features and benefits of the invention will now become more clear from a review of the following detailed description of illustrative embodiments and the accompanying drawings, wherein.

DETAILED DESCRIPTION OF PREFERRED EMBODIMENTS

Figure 1:
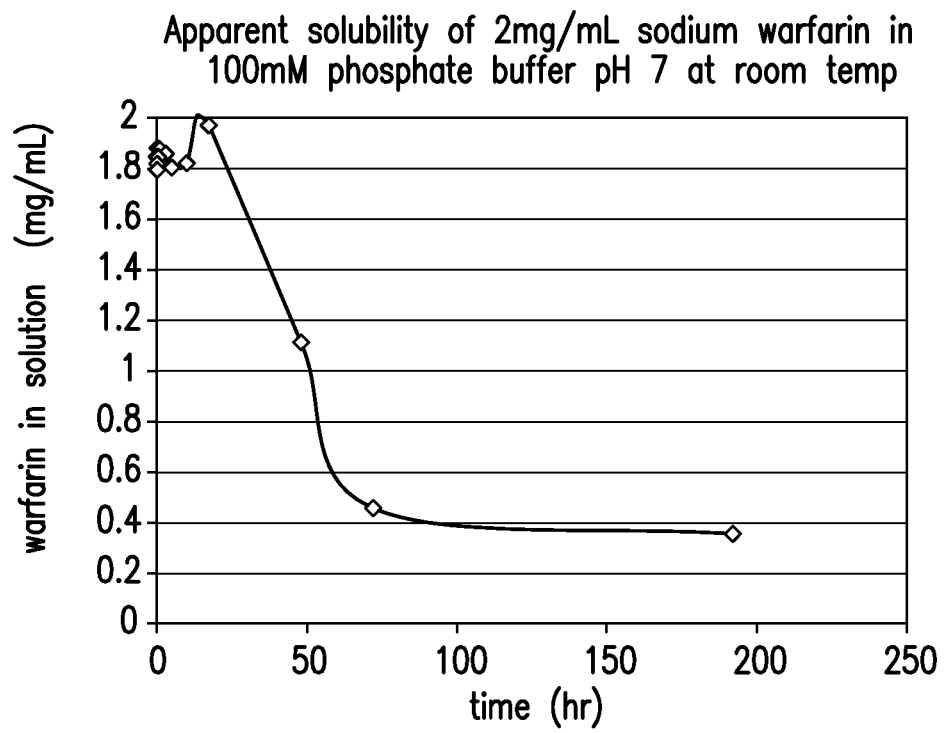
FIG. 1 is a graphic representation of the apparent solubility of warfarin sodium (2 mg/mL) in 100 mM phosphate buffer at pH 7 at room temperature.

The present invention relate to a stable liquid formulation of warfarin sodium and a method for preparing the same. Advantageously, the present warfarin sodium liquid formulation is stable in the long term and does not require lyophilization or reconstitution of lyophilized powder before use. Furthermore, the present warfarin sodium formulation can be administered orally, and therefore satisfies the need for the drinkable form of warfarin sodium.

As used herein, the term "active agent" can be understood to include any substance or formulation or combination of substances or formulations of matter which, when administered to a human or animal subject, induces a desired pharmacologic and/or physiologic effect by local and/or systemic action.

As used herein, the term "excipient" can be understood to include any inert substance combined with an active agent such as warfarin sodium to prepare a convenient dosage form and vehicle for delivering the active agent.

As used herein, the term "dose" and "dosage" can be understood to mean a specific amount of active or therapeutic agents for administration.

As used herein, the term "therapeutically effective amount" can be understood to include an amount of warfarin sodium that is effective to prevent or ameliorate a condition requiring an anticoagulant therapy.

According to the present invention, a stable warfarin sodium liquid formulation is provided as a mixture of glycerin, a pH buffer that provides a pH above 5, and optionally an alcohol. In a preferred embodiment, glycerin is included in an amount at least 20% v/v of the mixture. For a formulation with a pH less than 8, alcohol is preferably included in an amount at least 0.1% of the mixture by volume. The formulation can be provided for oral administration or for parenteral administration.

Advantageously, the warfarin sodium liquid formulation produced according to the present invention exhibits superior stability, with warfarin sodium degradation of about 5% or less over a period of one month at room temperature. In a further preferred embodiment of the invention, degradation of 2% or less is achieved under the same conditions. Such superior stability is achieved by providing warfarin sodium in solution with the specific excipients, including a pH buffer of pH above 5, glycerin, and an alcohol such as ethanol, at advantageous amounts.

WARFARIN SODIUM. Any pharmaceutical grade of warfarin sodium may be used. The choice of warfarin sodium may thus be dictated by economy. The amount of warfarin sodium included in the present liquid formulation is also dictated by the intended use. Generally, a dosage of about 0.1 mg/mL to about 20 mg/mL, preferably about 0.5 mg/mL to 10 mg/mL and more preferably about 1 mg/mL to 5 mg/mL, of warfarin sodium can be provided.

BUFFER SYSTEM. Any suitable buffer system which will act to buffer, that is, permit small variations of pH within, the warfarin sodium solution in the pH range above 5, and preferably about 8-9, can be employed. Among such buffer systems may be mentioned phosphate buffers such as sodium or potassium monobasic phosphates or di-basic phosphates as well as other pharmaceutically acceptable buffers. Mixtures of buffering agents can also be used. Other buffering agent, such as boric acid can also be used. Instead of, or in addition to, a buffer system, water can be used in the present formulation since water can provide a pH above 5. When water is present, use of a buffer is optional and is generally needed only when higher pH values are desired.

Although warfarin sodium has a very high level of apparent solubility in water, of greater than 7 g/mL, the protonated form of warfarin (pKa 5.05) has an equilibrium solubility of $1.28 \times 10^{-5}$ M (at ionic strength of 0.5). Thus, it has been unexpectedly found that the present formulation provides a long-term stability characterized by warfarin sodium degradation of 5% or less after a month at room temperature. Further, by providing a pH above 7, reversion of warfarin sodium in the solution back to warfarin is avoided, thus preventing precipitation of warfarin sodium from the solution in the long term, which may be attributable to the reversion of the warfarin anion to its protonated form. In a more preferred embodiment, pH of about 8 to 9, is provided. For example, a buffer close to a pH of about 8.3 can be used.

Stability of a 2 mg/mL solution of warfarin sodium in a 100 mM phosphate buffer at pH 7 at room temperature over approximately two days is provided in Table 1 and FIG. 1.

TABLE 1

Solubility of Warfarin Sodium in pH 7 Phosphate Buffer
Solubility of warfarin sodium with time for 2 mg/mL
in pH 7 phosphate buffer at room temperature (RT)

| Time hr | Warfarin concentration mg/mL |
|---|---|
| 0.017 | 1.84599 |
| 0.083 | 1.81907 |
| 0.167 | 1.79561 |
| 0.25 | 1.88043 |
| 0.333 | 1.84673 |
| 0.5 | 1.84355 |
| 1 | 1.8765 |
| 3 | 1.85841 |
| 5 | 1.80408 |
| 10 | 1.82153 |
| 13.5 | 2.0099 |
| 17.25 | 1.97 |
| 48 | 1.113 |
| 72 | 0.459 |
| 192 | 0.357 |
| 192 | 0.362 |

Figure 2:
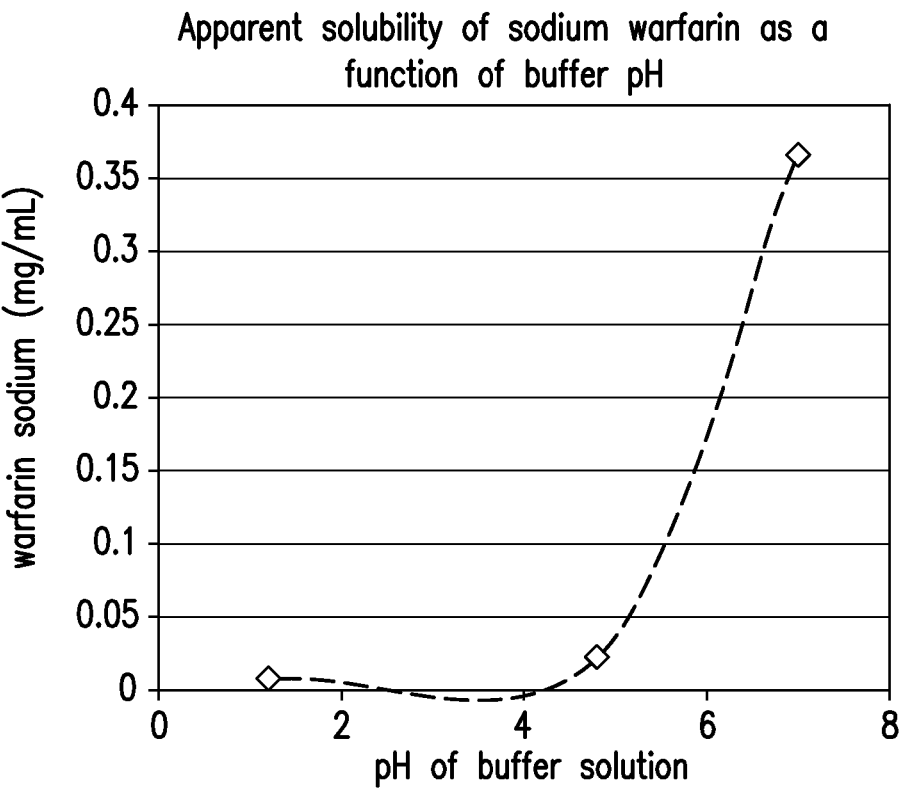
FIG. 2 is a graphic representation of apparent solubility of warfarin sodium as a function of buffer pH.

FIG. 2 provides apparent solubility of warfarin sodium at various pH buffer conditions at two days at room temperature.

Figure 3:
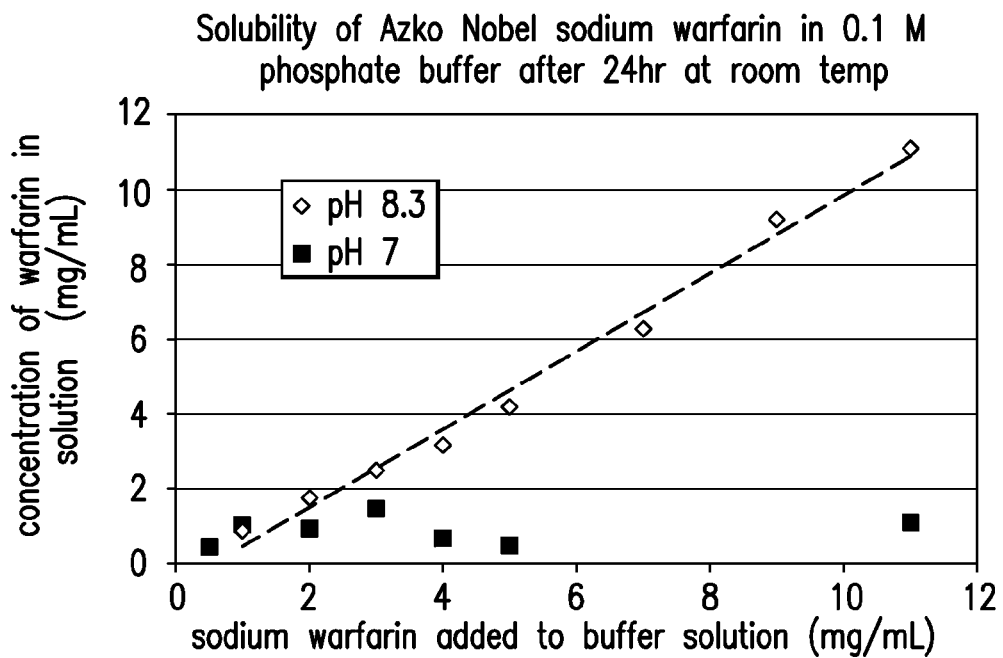
FIG. 3 is a graphic representation of the solubility of warfarin sodium in 0.1 M phosphate buffer after 24 hours at room temperature.

In a preferred embodiment of the present composition with a pH buffer of a pH between 8 and 9, it has been shown that the warfarin sodium solution remains free of precipitation for at least one month at room temperature. FIG. 3 compares the solubility of warfarin sodium in 0.1 M phosphate buffer after 24 hours at room temperature at pH 8.3 versus pH 7. As FIG. 3 and the Table 2 below show, improved solubility of warfarin sodium can be achieved by providing a pH greater than 7 if desired.

TABLE 2

Solubility of Warfarin Sodium in Phosphate Buffer
at pH 7 vs. pH 8
After 24 hrs at RT

| pH7 phosphate buffer | | pH8 phosphate buffer | |
|---|---|---|---|
| mg/mL warfarin added | Warfarin in solution mg/mL | mg/mL warfarin added | Warfarin in solution mg/mL |
| 0.5 | 0.452 | 1 | 0.9 |
| 1 | 1.035 | 2 | 1.8 |
| 2 | 0.935 | 3 | 2.5 |
| 3 | 1.476 | 4 | 3.2 |
| 4 | 0.679 | 7 | 6.3 |
| 5 | 0.485 | 9 | 9.2 |
| 11 | 1.094 | 11 | 11.1 |

While a phosphate buffer is most often described for use in the present warfarin sodium liquid formulation, it will be appreciated that other any buffer systems comparable to phosphate buffer may be used according to the present invention. For example, a boric acid buffer can be used in formulations for intravenous injection, although it may not be used in formulations for oral administration.

GLYCERIN. In preferred embodiments of the invention, glycerin is included in the warfarin sodium liquid formulation in an amount of least 20% (v/v) of the formulation. For example, glycerin can be included in an amount of about 20 to 93% of the formulation by volume. Such amount of glycerin is especially advantageous for providing self-preservation to the formulation given the lack of suitable preservatives available for the preferred pH range of about 7 or above. Glycerin also helps inhibit reprecipitation of warfarin out of the solution in buffer. In addition, glycerin provides various other functions and advantages. For example, because glycerin imparts a sweet taste, it can effectively disguise the taste of the drug for oral formulations without using any other sweeteners. When included in an amount of 20% or more, glycerin can also act as an antimicrobial or antibacterial agent.

ALCOHOL. The present composition can optionally include an alcohol, especially for a formulation with a pH below 8. Alcohol provides chemical stabilization to the formulation and helps inhibit reprecipitation of warfarin out of the solution in buffer. Any suitable pharmaceutically acceptable alcohol in an effective amount may be included. For an oral or a parenteral formulation, for example, ethanol or isopropyl alcohol (IPA) or other alkyl alcohols or benzyl alcohols can be used. When used, alcohol can be included in an amount effective to inhibit precipitation of warfarin up to about 20% of the formulation by volume.

In addition to warfarin sodium, a pH buffer, glycerin, and alcohol, any other suitable additives can be included in the present liquid formulation. For example, pepsin can be included to enhance solubility of warfarin sodium in the formulation. In one embodiment, pepsin can be included in an amount of about 0 to 0.16 mg/mL (0 to 960 units/mL) in the present formulation. A surfactant such as TWEEN® and SLS can also be included. For an oral formulation, a flavorant or taste enhancer can also be included. A sweetener is particularly advantageous for masking the drug taste of warfarin sodium. Commonly used natural or artificial sweeteners such as saccharin, sorbitol, mannitol, liquid sugar, and TWEEN® 80 are all compatible with the present formulation and can effectively enhance the taste of the formulation. A cellulose such as hydroxyproxymethyl cellulose (HPMC) or PVP, PEG, PG, a gum such as Xantham gum, an oil, and/or a fatty acid can also be included in the formulation. Table 3 shows compatibility of warfarin sodium with certain excipients, as characterized by % degradation of warfarin sodium in pH 8 buffer after one month at 50° C.

TABLE 3

Amount of Warfarin Sodium Degradation in pH 8 Buffer with Excipients (after 1 month at 50° C.)

| Excipient | % degradation of warfarin sodium | Color change |
| --- | --- | --- |
| Saccharin (0.5% w/v) | 3.3 | Light yellow |
| Sorbitol (50% v/v) | 2.9 | Light yellow |
| Glycerin (50% v/v) | 1.5 | |
| Mannitol (5% w/v) | 1.9 (after 384 hr) | Light yellow |
| Ethanol (50% v/v) | 0.7 | |
| Liquid sugar (50% v/v) | 2.4 (after 312 hr) | Yellow |
| HPMC (1% w/v) | 0.8 | |
| TWEEN® 80 (0.5% v/v) | 5.1 | |
| Phosphate buffer pH 8 | 1.4 | Light yellow |

Oral formulations produced according to the present invention will normally be in the form of a solution. When a thicker or thinner product is desired, however, an additive can be added accordingly. For instance, an edible thickener that is compatible with the present product can be included to produce a syrup-like product. Additives such as liquid sugar, HPMC, PVP and Xanthan gum also increase the viscosity of the solution and therefore can be used to produce a thicker product.

Warfarin is known to form complexes with mercury, cadmium, zinc, and copper that have variable toxicities (see Pharmazie 49: 856-857 (1994)). Thus, in one embodiment of the invention, a chelating agent capable of neutralizing trace metals can be added. Ethylene diamine tetra-acetic acid (EDTA) is a particularly advantageous additive that prevents warfarin sodium from degrading in the formulation. By neutralizing toxic metal complexes and enhancing warfarin sodium stability, EDTA can also reduce variability of patient response to the warfarin product made according to the present invention. In addition to EDTA, other chelating agents such as TPGS can be used.

Because the present formulation may undergo a slight color change and show a slightly yellow color depending on the excipients used, an artificial color can be added to mask any such color change. For example, when the formulation is stored in a clear glass container for an extended time, addition of an artificial color such as yellow or orange color can be desired. For example, color additives such as yellow #5 or yellow #6 can effectively mask any color change while not adversely affecting stability of the formulation. Other colors, such as red or purple, or any other color desired for the product, can also be used. These colors have been tested and were shown to be compatible with warfarin sodium.

In addition, because the present warfarin sodium formulation is similar to the conventional tablet form in effectiveness and absorption, any other pharmaceutically effective agent that can be administered with the conventional warfarin sodium tablet can also be administered with the present warfarin sodium formulation. Non-limiting examples of other pharmaceutical agents compatible with warfarin sodium and that can be co-administered with the present formulation include other anti-coagulants or coagulation inhibitory agents as well as any other therapeutic agents.

The warfarin sodium liquid formulation according to the invention can be provided in any amount in any suitable packaging, including plastic and glass bottles and containers containing single or multi doses of the product. Enclosures for the packaging can also be varied as desired. A simple cap enclosure can be most economical, and a dropper-in-cap enclosure system can be used for more accurate delivery of the product. Hence, a packaging bottle with a dropper can provide a convenient and accurate measurement of the product and can be more suitable when used directly by patients, while a simple capped bottle may be preferred for physician or hospital uses. A manufacturer may choose any desired, cost-effective packaging.

Because warfarin sodium is sensitive to the light, a glass container with color, such as brown color, is preferred over a clear glass container. For example, the warfarin sodium composition shows better long-term stability when stored in a brown glass bottle compared to a clear glass bottle, which allows greater light penetration. When the present composition is provided in a colored glass bottle, a chelating agent such as EDTA or TPGS can further enhance the composition's long-term stability since a chelating agent neutralizes silicon metal complexes that can be formed when the composition is stored in a glass bottle.

In a further preferred embodiment of the invention, the warfarin sodium composition is provided in a container made of a high-density polyethylene (HDPE) material, which eliminates any chemical reaction of warfarin sodium with free silicon that may occur in a glass bottle. As further explained with respect to the prototype formulations in the Examples, a composition in a HDPE container retains greater long-term stability than a composition contained in a container made of a non-HDPE material, such as glass.

Another advantage of the present warfarin sodium liquid formulation over the conventional oral tablet and injectable product is its simple process of preparation. The present formulation is produced by simply mixing an amount of warfarin sodium, a pH buffer, glycerin, and alcohol, and any other optional additives, in a solution, and does not require any pre- or post-treatment steps or other complicated procedures. In particular, the present process for preparing a stable warfarin sodium liquid formulation comprises dissolving an amount of warfarin sodium in a solution of excipients comprising a pH buffer, such as a phosphate buffer, and glycerin,. Optionally, other additives such as an alcohol, a sweetener, HPMC, pepsin, or a chelating agent can also be added. The produced formulation can then be packaged in any suitable container.

The warfarin sodium liquid formulation prepared according to the present invention is useful for providing an anti-coagulant therapy. Thus, the invention also provides an advantageous method for providing an anti-coagulant therapy to a patient by administering a therapeutically effective amount of warfarin sodium to the patient. For example, about 0.1 mg/mL to about 10 mg/mL of warfarin sodium can be administered per day to provide an effective anti-coagulant therapy.

Therefore, the present invention provides a simple and efficient process for producing a liquid form of warfarin sodium product. Manufacturers will appreciate the simplicity and cost-effectiveness of the process, while physicians and consumers will appreciate a stable liquid alternative to the conventionally available tablet and injectable forms of the drug that does not require complicated reconstitution steps or vigilant monitoring before use. It is also easy for dose adjustments, which is usually required during anticoagulate therapy.

EXAMPLES

The following examples are illustrative only and should not be interpreted as limiting.

Materials, Instruments, Analysis Conditions

In the following examples, a number of columns and mobile phases were evaluated. Because warfarin sodium has a number of potential functional groups, including ketone, phenyl, and enolic type of groups, its functionality can interact with different stationary phases, such as C18, Phenyl orcyano-containing phases, to display separations. All these phases were investigated using different mobile phases.

The experimentation was performed on Hewlett Packard 1100 series HPLC systems.

The following chromatographic conditions were used for experimental studies.

| | |
|---|---|
| Mobile Phase | 25% Acetonitrile, 75% Water, 1% Acetic Acid |
| Detection | 260 nm and 280 nm |
| Flow Rate | 0.8 mL/min |
| Injection Volume | 10 µL |
| Column Temp. | 40° C. |
| Run Time | About 20–30 minutes |

The drug product was subjected to different conditions in an attempt to produce partial degradation by feasible and realistic pathways. The placebo and preservative standards were individually stressed in an analogous manner. Test solutions for evaluation of specificity were prepared according to the procedure described below.

Warfarin sodium was weighed to the desired weight. This was transferred to glass tubes and dissolved in either buffer or milliQ water. To this solution was added a number of various excipients suitable for use in oral solutions and syrups. Placebos were created using either buffer or water with excipients. These mixtures were kept at either ambient conditions or at an accelerated storage condition of 50° C. Periodically, samples were removed from these tubes for analysis.

Example 1.

Comparative Study of pH Buffer Systems

Figure 4:
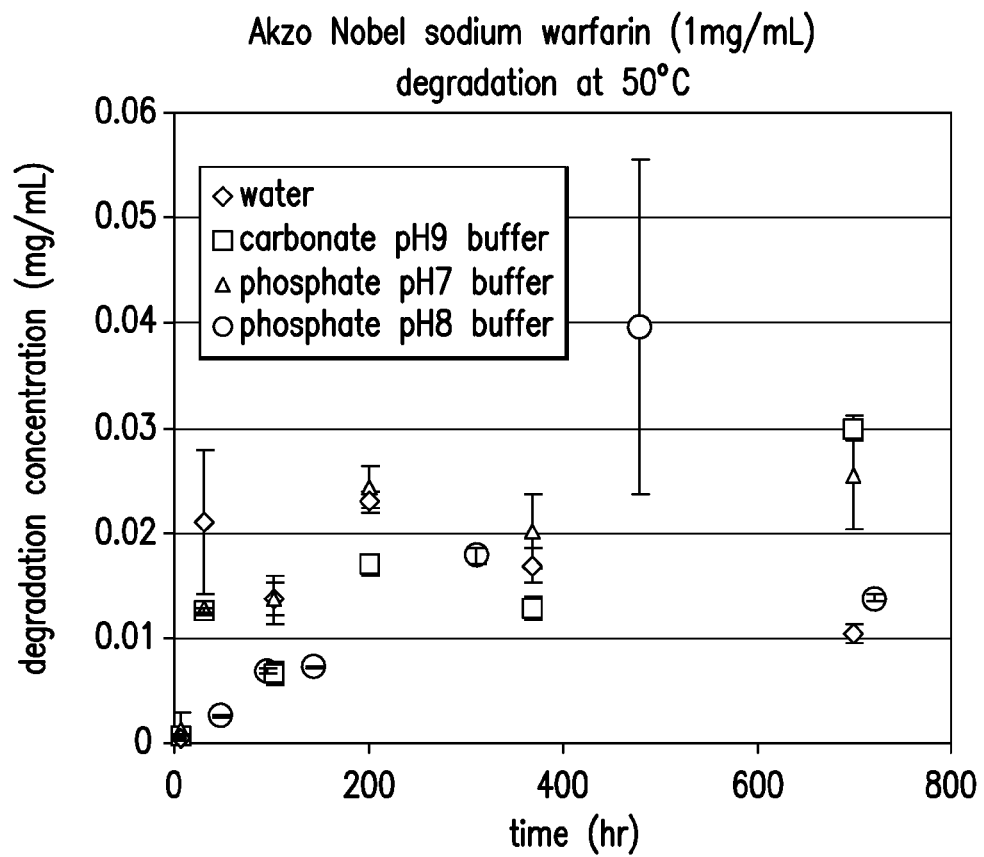
FIG. 4 is a graphic representation of the degradation amount of warfarin sodium (1 mg/mL) at 50° C.

A comparative study of various buffer pHs was conducted to determine the most preferred pH level for the oral formulation of the present warfarin sodium composition. The study evaluated the stability of a warfarin sodium solution at 1 mg/mL warfarin sodium concentration for 1 month at 50° C. in phosphate buffers at pH 7 and 8, a carbonate buffer at pH 9, and water. Warfarin sodium was most stable in water, followed by the phosphate buffer at pH 8, then at pH 7, and finally carbonate buffer at pH 9. The results of the study are shown in FIG. 4. Based on these studies, warfarin sodium solutions buffered at pH 8 or in water were considered most resistant to long term degradation.

After approximately 1 week at 50° C., the warfarin sodium solutions in pH 9 carbonate buffer underwent a slight yellowing which grew darker with time. A similar color change was observed for the warfarin sodium solutions in pH 8 phosphate buffer after approximately 1 month at 50° C. The color change was observed regardless of the source of warfarin sodium.

Example 2.

Comparative Study of Excipients

Figure 5:
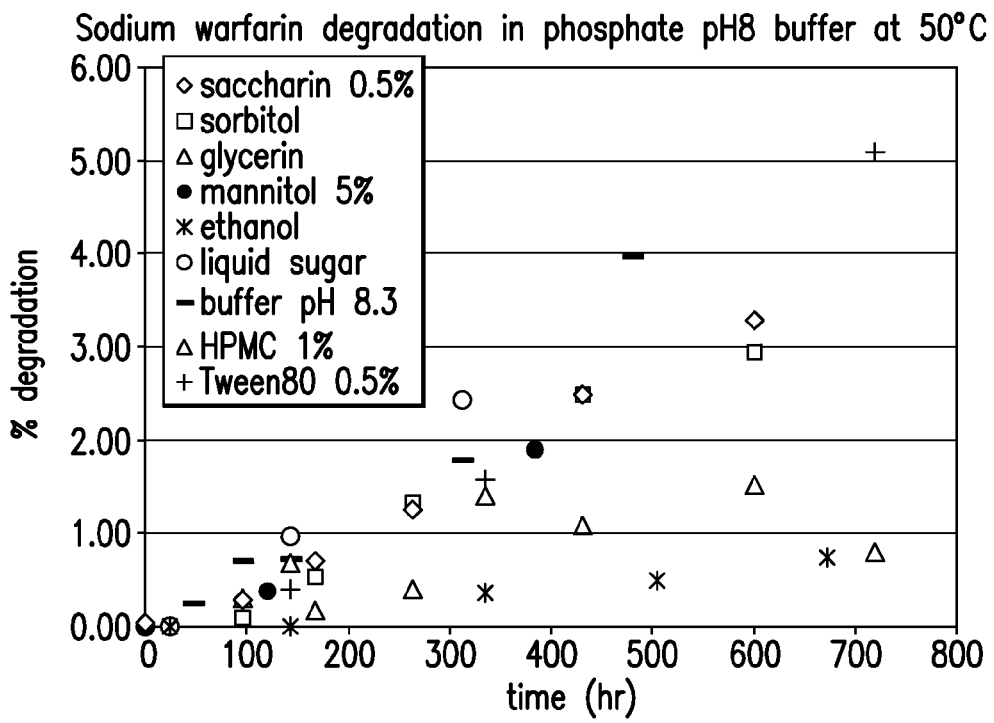
FIG. 5 is a graphic representation of warfarin sodium degradation in pH 8 phosphate buffer at 50° C.

The compatibility of excipients that can be used in a warfarin sodium oral solution was evaluated, using a number of excipients typically used in oral liquid formulations. The excipients were mixed at a 1:1 ratio with warfarin sodium dissolved in phosphate buffer at pH 8.3 (100 mM). The final warfarin sodium concentration in these mixtures was at 1 mg/mL, and the excipients used were either in liquid form or made into aqueous solutions (w/v). The results of the stability screening after 1 month at 50° C. for the most compatible excipients are shown in FIG. 5. These excipients include ethanol, glycerin, HPMC (1%), mannitol, sorbitol, liquid sugar, saccharin (0.5%), and TWEEN® 80 (0.5%). The result of using the pH 8.3 buffer alone without any other excipient is also shown.

As FIG. 5 shows, HPMC, ethanol, and glycerin, all resulting in less than 2% degradation, were the most effective excipients in reducing warfarin sodium degradation. After 1 month at 50° C. warfarin sodium in solution with sorbitol, saccharin, and sucralose were only slightly more stable than with the buffer alone. In addition, warfarin sodium in solution with saccharin, liquid sugar, mannitol, and sorbitol underwent a slight yellow color change. No color change was observed, however, in a 1:1 mixture with glycerin or ethanol. Because the comparative study of pH buffers (Example 1) demonstrated good stability of warfarin sodium in water, an excipient screen was duplicated using water instead of pH 8 buffer. Interestingly, however, almost all the excipients demonstrated significantly higher degradation of warfarin in water compared to the warfarin degradation in pH 8 buffer, therefore suggesting that a buffer such as a phosphate buffer plays a role in stabilizing warfarin sodium in solution.

Based on these excipient screens, a combination of glycerin, pH 8 phosphate buffer, and ethanol was predicted to demonstrate good long-term stability.

Example 3.

Prototype Formulations

A series of prototype formulations were prepared to evaluate various combinations of the stability indicating excipients. These formulations were studied at both room temperature and in accelerated stability conditions at 50° C. for one month. Additionally, formulations made in both water and a pH 8 buffer were studied to determine the solvent system that provides the most stability to warfarin sodium.

A. Formulations 1-2

The following Formulations 1 and 2 compares the presence of glycerin (Formulation 1) and lack thereof.

| | Formulation 1 | |
|---|---|---|
| Excipient | Amount per 20 mL | % of formulation |
| warfarin sodium | 5 mg | 0.25 mg/mL |
| water or pH 8 phosphate buffer | 15.1 mL | 75.5% v/v |
| glycerin | 4 mL | 20% v/v |
| HPMC-K4 | 400 µL of 0.1% solution ≈ 0.4 mg | 0.002% w/v |
| TWEEN® 80 | 100 µL | 0.5% v/v |
| ethanol | 200 µL | 1% v/v |
| saccharin | 400 µL of 0.1% solution ≈ 0.4 mg | 0.002% w/v |

| Formulation 2 | | |
|---|---|---|
| Excipient | Amount per 20 mL | % of formulation |
| warfarin sodium | 5 mg | 0.25 mg/mL |
| water or pH 8 phosphate buffer | 14.9 mL | 74.5% v/v |
| sorbitol | 4 mL | 20% v/v |
| HPMC-K4 | 400 µL of 0.1% solution ≈ 0.4 mg | 0.002% w/v |
| TWEEN® 80 | 100 µL | 0.5% v/v |
| ethanol | 200 µLL | 1% v/v |
| saccharin | 400 µL of 0.1% solution ≈ 0.4 mg | 0.002% w/v |

Formulation 1 was found to have a much lower viscosity compared to Formulation 2 because of the difference in viscosity of sorbitol and glycerin. It was observed that both formulations underwent a slight yellow color change, which may be due in part to storage in clear glass tubes. Formulation 1 (in water) initially had a pH 7.5, which, after 792 hours at 50° C., increased to pH 8-9. Formulation 2 (in water), which had an initial pH of 7.2, also underwent a pH increase to pH 8-9. However, in pH 8 buffer, Formulation 1 and 2 had no significant change in pH after 696 hours at 50° C. Degradation of HPMC, however, seemed to cause a cloudy precipitation in Formulation 2 made with the pH 8 buffer.

Figure 6:
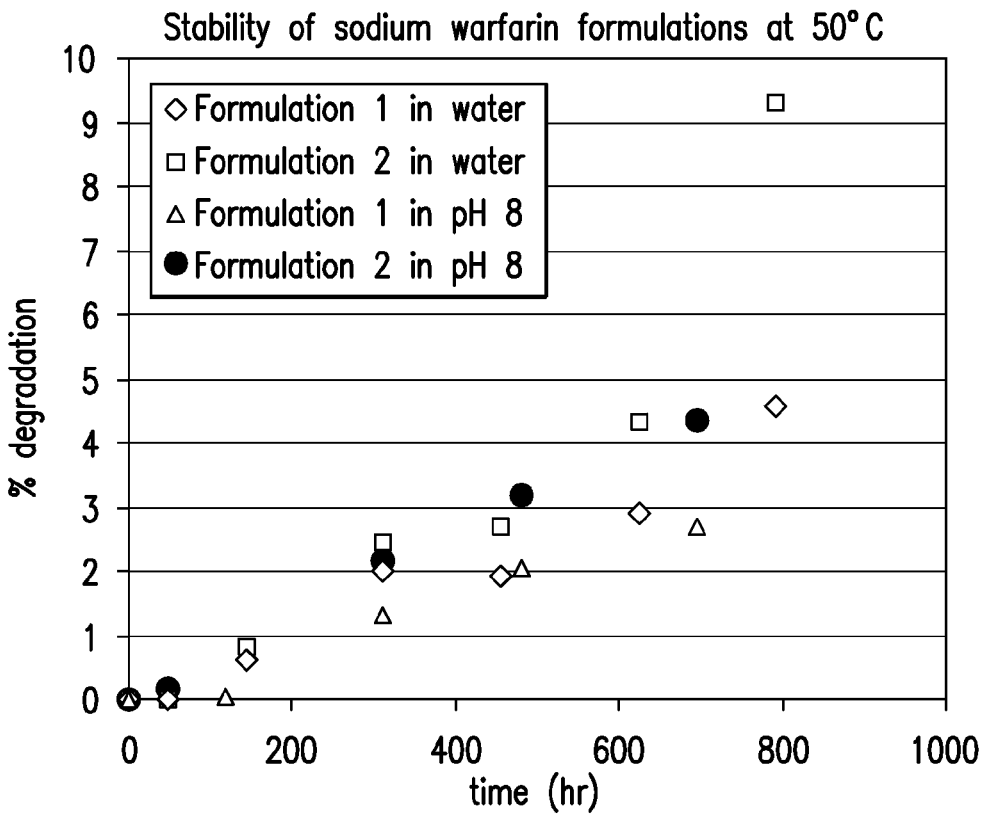
FIG. 6 is a graphic representation of the stability of warfarin sodium prototype formulations (Formulations 1 and 2) at 50° C.

The comparison of Formulations 1 and 2 showed that Formulation 1 is more stable than Formulation 2 either in water or a pH 8 buffer. The results are graphically shown in FIG. 6, which shows the amount of degradation (%) of warfarin sodium in each formulation. Hence, glycerin is more compatible with warfarin sodium than sorbitol in these formulations, and the phosphate buffer was able stabilize warfarin sodium better than water.

B. Formulations 3-4

The following two formulations, Formulations 3 and 4, were made with phosphate buffer to prevent changes in pH observed in the formulations made with water. The amount of warfarin sodium was also increased from 0.25 mg/mL to 1.25 mg/mL. TWEEN® 80 and saccharin were eliminated in these formulations based on (i) the color change in the solution containing saccharin and (ii) the accelerated warfarin degradation in the solution containing TWEEN® 80, observed during the excipient screening. As alternatives to these excipients, liquid sugar and mannitol were used.

| Formulation 3 | | |
|---|---|---|
| Excipient | Amount per 20 mL | % of formulation (w/v or v/v) |
| HPMC-K4 | 200 µL of 0.1% solution ≈ 0.2 mg | |
| phosphate buffer pH 8.3 | 13.8 mL | 69% v/v |
| warfarin sodium | 25 mg | |
| glycerin | 4 mL | 20% v/v |
| ethanol | 1 mL | 5% v/v |
| mannitol | 1 mL of 10% solution ≈ 0.1 g | 5% v/v |

| Formulation 4 | | |
|---|---|---|
| Excipient | Amount per 10 mL | % of formulation (w/v or v/v) |
| HPMC-K4 | 200 µL of 0.1% solution ≈ 0.2 mg | |
| phosphate buffer pH 8.3 | 13.8 mL | 64% v/v |
| warfarin sodium | 25 mg | |
| glycerin | 4 mL | 20% v/v |
| ethanol | 1 mL | 5% v/v |
| liquid sugar | 2 mL of 10% solution | 10% v/v |

Figure 7:
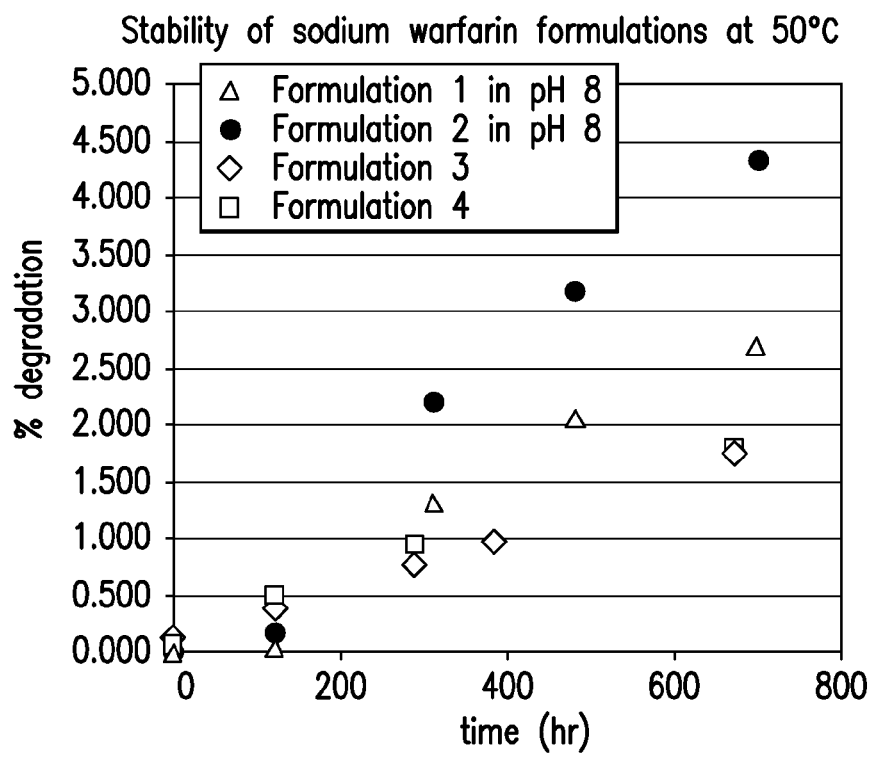
FIG. 7 is a graphic representation of the stability of warfarin sodium prototype formulations (Formulations 1-4, with Formulations 1-2 in pH 8 buffer) at 50° C.

Containing a phosphate buffer, glycerin and ethanol, both Formulation 3 and 4 were found to be more stable than Formulations 1 and 2. FIG. 7 compares warfarin degradation % of Formulations 1-4. The concentration of warfarin sodium in these formulations was also constant over one month at room temperature, demonstrating these formulations keep warfarin sodium in solution without precipitation reversion. However, both Formulation 3 and 4 underwent a yellow color change after 3-5 days at 50° C., which may be attributed in part to the sugars used, and to the storage in clear glass tubes.

C. Formulation A-B

The following excipients were used to form Formulation A:

| Excipient | v/v | w/v (g/100 mL) | Per unit dose (1 mL) |
|---|---|---|---|
| Glycerin | 35% | 43.75% | 0.4375 g |
| Alcohol (dehydrated) | 8% | 6.3% | 0.063 g |
| Phosphate buffer pH 8.2 (10 mM) | 57% | 57% | 0.57 g |
| Warfarin sodium | | 0.1%* | 0.001 g |

Figure 8:
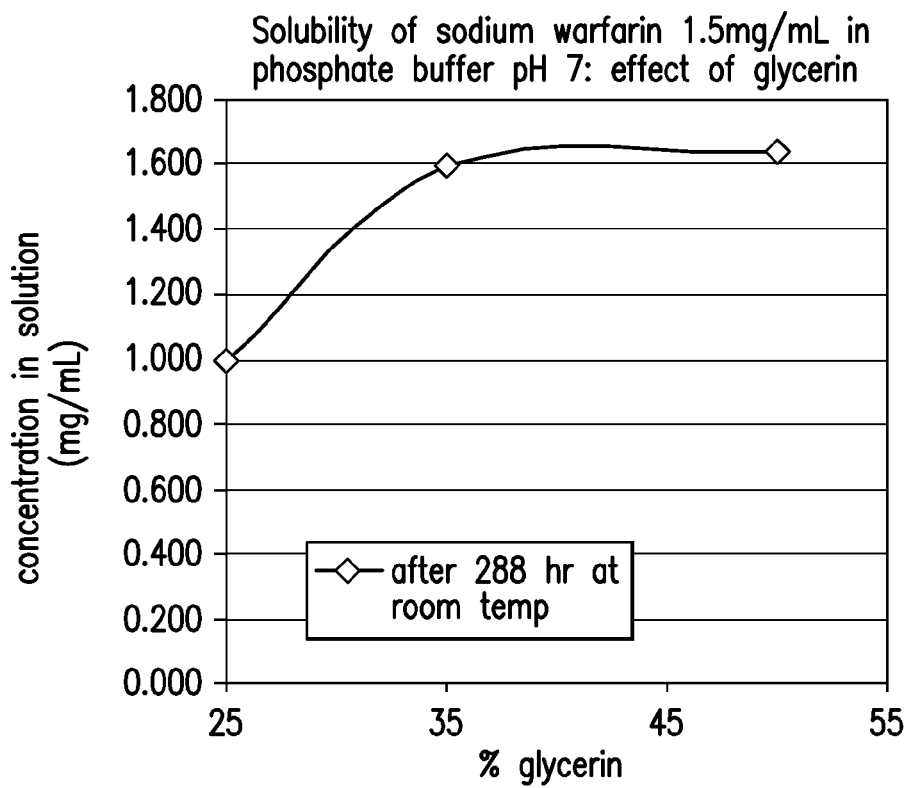
FIG. 8 is a graphic representation of the solubility of warfarin sodium (1.5 mg/mL) in pH 7 phosphate buffer versus the amount of glycerin.

*corrected for isopropyl alcohol content (8.0–8.5%) in warfarin sodium clathrate Formulation A was found to have a viscosity similar to that of Formulation 1 and was easily aliquoted from a dropper or pipette. Advantageously, because Formulation A has a sweet taste, the taste of the drug can be effectively masked without an additional sweetener or flavor. Further, it has been advantageously found that increasing the amount of glycerin to 35% by volume in the warfarin sodium solution made with a buffer at pH 7 prevents precipitation of warfarin. As previously explained, more warfarin precipitation was observed in a solution made with a pH 7 buffer compared to one made with a pH 8 buffer. Hence, it has been found that including glycerin in the amount of at least 35% would significantly improve solubility and stability of warfarin sodium in a liquid formulation. FIG. 8 demonstrates that increasing the amount of glycerin in the solution to 35% or more prevents warfarin precipitation.

Furthermore, a solution containing glycerin in the amount of 35% or more by volume would have an effective antimicrobial properties, since glycerin is an effective antimicrobial when used at concentrations higher than 20% v/v as explained in the Handbook of Pharmaceutical Excipients, 3rd Ed. Similarly, use of alcohol at concentrations greater than 10% v/v also provides an antimicrobial effectiveness, and the amounts of glycerin and alcohol may be adjusted to provide the desired antimicrobial activity. Formulations containing 35% glycerin by volume and 0-8% alcohol, such as Formulation A, were shown to provide an effective antimicrobial activity. When a higher amount of alcohol is included, for example 10% or more by volume, a lesser amount of glycerin can be sufficient for antimicrobial effectiveness.

Figure 9:
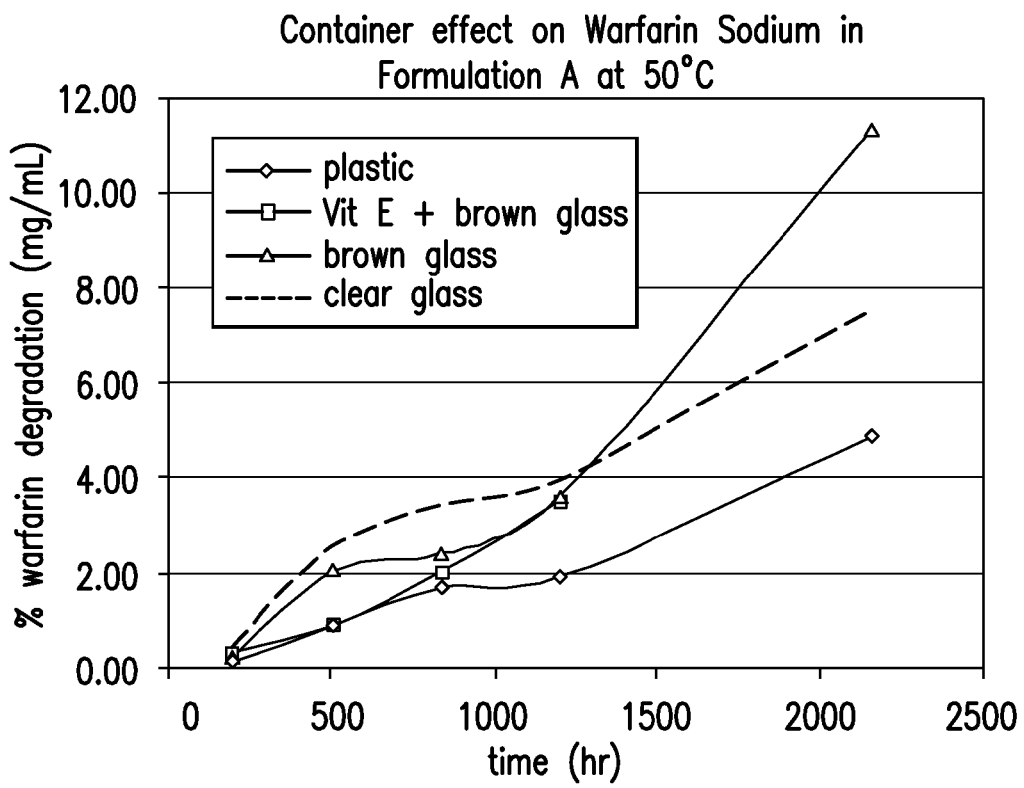
FIG. 9 is a graphic representation of the effect of container material on warfarin sodium stability.

The effect of the container material was also tested over a period of about 3 months at 50° C. Clear glass tubes, brown glass bottles (with and without Vitamin E), and plastic bottles were used to determine any changes in warfarin sodium stability and solubility in Formulation A. The result of the study is presented in Table 4 and graphically in FIG. 9A.

TABLE 4

Stability of Formulation A in Various Containers Stored at 50° C. over ~50 days

| time hr | plastic warfarin sodium % deg | Vitamin E + brown glass warfarin sodium % deg | brown glass warfarin sodium % deg | clear glass warfarin sodium % deg |
|---|---|---|---|---|
| 192 | 0.181 | 0.373 | 0.248 | 0.451 |
| 504 | 0.946 | 0.915 | 2.064 | 2.557 |
| 840 | 1.7056 | 2.0365 | 2.4349 | 3.4446 |
| 1200 | 1.932 | 3.5147 | 3.6013 | 3.9773 |

The degradation of warfarin sodium was accelerated in clear glass containers, perhaps caused by light sensitivity, or saponification of the glass at pH>8. The antioxidant vitamin E clearly reduced the amount of degradation of warfarin sodium in brown glass bottles up to 1 month at 50° C., and may be useful if plastic bottles cannot be used. Although vitamin E is used as an example, other antioxidants can also be used.

Interestingly, when this same study was performed at 40° C., there was little difference between the containers, although warfarin sodium glass containers were slightly more stable than plastic.

The ability of ethylene diamine tetra-acetic acid (EDTA) to reduce the amount of degradation was also studied with a sample of Formulation A that had been stored at 50° C. for 504 hours in a plastic bottle. This sample was transferred to two clear glass tubes. EDTA (0.02 mg/mL) was added to one glass tube, and the other tube served as control without EDTA. Both tubes were returned to another 528 hours of storage at 50° C. At the end of the study, a visual comparison of both tubes demonstrated that the addition of EDTA resulted in less color change than the control tube without EDTA. The actual % degradation of warfarin was measured as shown in Table 5. These results suggest that EDTA can reduce the amount of warfarin degradation stored in glass containers.

TABLE 5

Effect of EDTA in Warfarin Sodium Stability

| | % Degradation of warfarin | Temp (° C.) | Time (hr) |
|---|---|---|---|
| Formulation A with EDTA | 1.74 | 50 | 528(504) |
| Formulation A no EDTA | 2.90 | 50 | 528(504) |

Figure 10:
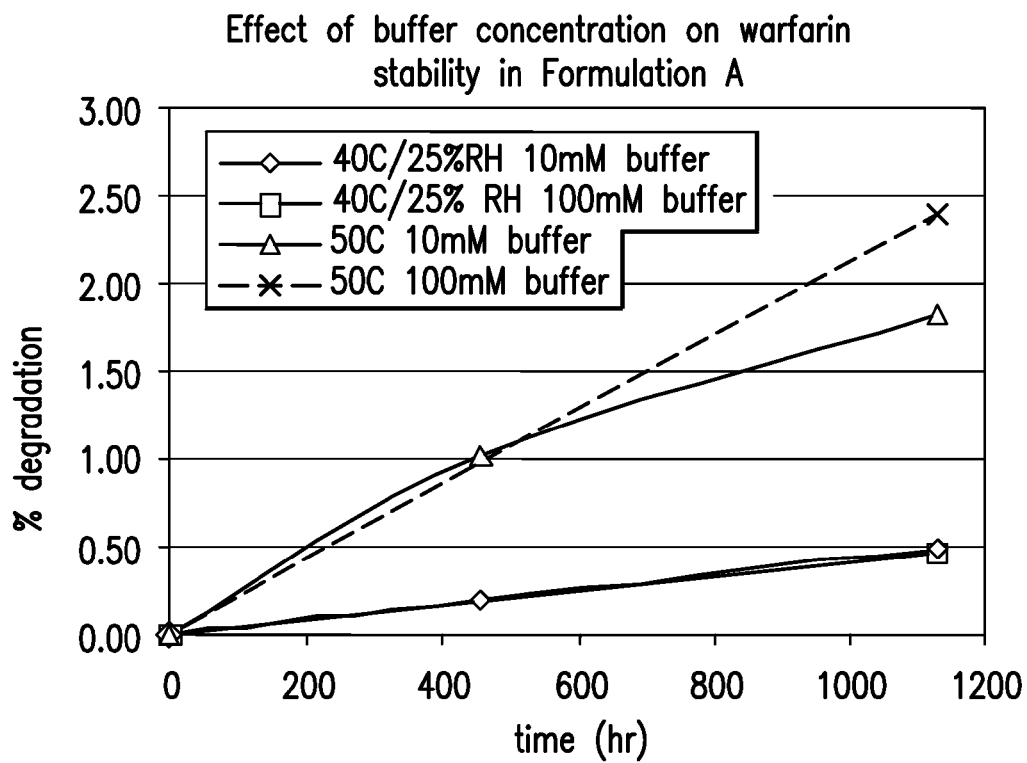
FIG. 10 is a graphic representation of the effect of buffer concentration on warfarin sodium stability.

The effect of phosphate buffer concentration was also investigated. Formulation A was prepared using either 10 or 100 mM phosphate buffer at pH 8.2, and these formulations were then studied at 40 and 50° C. The data presented in FIG. 10 show no significant difference between the 100 mM and 10 mM buffers at 40° C., although a difference was observed at 50° C.

Warfarin settlement out of the solution during storage was also evaluated. In order to determine if warfarin sodium in Formulation A would settle out of the solution, an evaluation of warfarin concentration at various depths in a container was performed. A 70 mL sample which had been at ambient conditions for over two months with little to no disturbance was used to conduct this assay. Two aliquots from each of three depths, 5, 40 and 65 cm depths, were removed and analyzed. No significant difference in warfarin concentration was observed between the samples of these depths.

A formulation with the same excipients used in Formulation A, but for a lower warfarin dose was developed as Formulation B, with a strength of 0.5 mg/mL and containing the same ratio of excipients as Formulation A.

To mask any color change that may be present, for example when the solution is stored in a clear glass container for an extended time, an artificial color such as yellow or orange color may be added to the solution. The effect of a color additive was studied with Formulation B that was stored at an accelerated condition of 40-50° C. and 75% relative humidity (RH) over a three-month period. The study showed that an artificial color additive may be used without an adverse effect on stability. There was no significant difference in stability between the formulations with and without a color additive for a sample stored at 40° C.

The compatibility of different packaging systems with the present liquid formulation was also evaluated using a cap packaging with an attached dropper enclosure and a cap without a dropper. This study was performed under storage conditions of 40° C. and 75% relative humidity for a period of two months. After two months, there was no significant difference between samples enclosed with the cap with attached dropper and those enclosed with the cap only.

Example 4.

Dissolution of Warfarin Sodium Tablet vs. Solution at pH 1.5

A study was performed to compare the characteristics of an oral warfarin sodium solution prepared according to the invention and those of a generic commercial tablet (manufactured by Barr Lab) of the same strength in a simulated gastric fluid. A 250 mL volumetric flask was used to simulate the capacity of stomach gastric volume, and a pH 1.5 HCl buffer (0.8% NaCl, 0.04% $CaCl_2$) was used for the simulated gastric fluid (SGF).

With a dose of 1 mg, both the tablet and oral solution had the same concentration of warfarin sodium in the SGF (see Table 6). Furthermore, no precipitation of warfarin sodium was observed after 24 hours at room temperature for either the solution formulation or the tablet.

A second experiment was performed to evaluate the effect of pepsin on solubility of warfarin sodium API in the SGF. A saturated solution of crystalline warfarin sodium was created by adding 5 mg of pure warfarin sodium into the SGF containing 1 mg of warfarin sodium (tablet or oral solution formulation). The amount of warfarin sodium in the solution was measured by HPLC and showed that neither the tablet nor the solution completely solubilized the additional warfarin sodium (see Table 6). However, when these solutions were prepared with pepsin (approximately 2400 units/mL pepsin (Sigma-Aldrich #P-7125; 600 units/mg)), no precipitation was observed for either formulation. The concentrations of warfarin sodium measured after 24 hours from both flasks (tablet and oral solution) were also close to the expected concentration of 0.024 mg warfarin per mL.

Finally, in order to determine the minimal amount of pepsin to effect solubilization of crystalline warfarin sodium in the SGF, the amount of pepsin was increased from 0 to 0.16 mg/mL (or from 0 to 960 units/mL). At 6 mg dose, warfarin sodium was observed to precipitate out of solution after 24 hours when no pepsin was present. However, even at the lowest concentration of pepsin evaluated (19.2 units/mL), no precipitation was observed for either the tablet or oral solution of warfarin sodium. These results suggest that, regardless of the excipients used in either the tablet or oral solution, use of pepsin can prevent precipitation of warfarin sodium in the gastric cavity.

TABLE 6

Solubility of Warfarin Sodium Solution vs. Tablet Amount of warfarin sodium in solution at pH 1.5 (using 250 mL volume flask for gastric volume)

| Formulation type | 1 mg dose Expected concentration~ 0.004 mg/mL | Without pepsin 1 mg dose + 5 mg Expected concentration~ 0.024 mg/mL | With pepsin 1 mg dose + 5 mg Expected concentration~ 0.024 mg/mL |
|---|---|---|---|
| Barr tablet | 0.004 | 0.013 | 0.025 |
| Liquid formulation | 0.004 | 0.009 | 0.026 |

What is claimed is:

1. A liquid composition comprising warfarin sodium as an active ingredient, glycerin in an amount effective to act as a stabilizer and a preservative and water or a pH buffer providing a pH above 5, wherein the amount of warfarin sodium in the composition that is degraded after at least 1 month at room temperature is about 5% or less.

2. The composition according to claim 1, further comprising an alcohol in an amount sufficient to stabilize the composition and help inhibit precipitation of warfarin.

3. The composition according to claim 2, wherein the glycerin is present in an amount of about 20 to 93% of the composition by volume and the alcohol is present in an amount of about 0.1 to 20% by volume.

4. The composition according to claim 3, wherein the composition is an orally or a parenterally administratable composition.

5. The composition according to claim 4, further comprising a pharmaceutically acceptable pH buffer, in an amount sufficient to provide a pH of about 5 to 9.

6. The composition according to claim 5, wherein the pH buffer is a phosphate buffer.

7. The composition according to claim 4, wherein the alcohol is an alkyl alcohol or a benzyl alcohol.

8. The composition according to claim 4, further comprising at least one of a chelating agent, a sweetener, pepsin, albumin, a surfactant, a cellulose, such as hydroxyproxymethyl cellulose (HPMC) or povidone (PVP), a polyethylene glycol (PEG), propylene glycol (PG), a gum, an oil, a fatty acid, and an antioxidant.

9. The composition according to claim 8, wherein the sweetener comprises saccharin, sorbitol, mannitol, liquid sugar, or combinations thereof, the chelating agent comprises ethylene diamine tetra-acetic acid (EDTA) or TPGS, and the antioxidant comprises vitamin E.

10. The composition according to claim 3, wherein warfarin sodium is present in an amount of about 0.1 mg/mL to about 20 mg/mL.

11. The composition according to claim 4, wherein the amount of warfarin sodium is 1 mg/mL.

12. The composition according to claim 4, wherein the orally administratable composition is a solution, a syrup, an elixir, or a suspension.

13. The composition according to claim 4, wherein the amount of warfarin sodium in the composition that is degraded after 1 month at room temperature is about 2% or less.

14. The composition according to claim 3, further comprising an agent that provides an antimicrobial activity.

15. The composition according to claim 1, wherein the composition is provided in a container comprising high-density polyethylene (HDPE).

16. The composition according to claim 1, which further comprises EDTA, wherein the composition is provided in a brown-colored glass bottle.

17. A method for preparing a stable liquid composition that includes warfarin sodium as an active ingredient, which comprises providing glycerin in the composition in an amount effective to act as a stabilizer and a preservative and providing the composition with a pH above 5, wherein the composition is sufficiently stable such that amount of warfarin sodium in the composition that is degraded after 1 month at room temperature is about 5% or less.

18. The method according to claim 17, which further comprises providing an alcohol in an amount sufficient to stabilize the composition and help inhibit precipitation of warfarin sodium.

19. The method according to claim 17, wherein glycerin comprises at least 20% of the composition by volume and the pH is achieved by adding water or a pH buffer to the composition.

20. The method according to claim 19, wherein the stable liquid composition is an oral composition and wherein the pH buffer is a phosphate buffer.

21. The method according to claim 20, wherein the pH provided by the pH buffer is between about 5 and 9.

22. A method for providing an anti-coagulant therapy to a subject in need thereof, which method comprises administering a therapeutically effective amount of the composition of claim 1 to the subject.

23. The method according to claim 22, wherein the amount of warfarin sodium administered per day is about 0.1 mg/mL to about 20 mg/mL.

24. The method according to claim 23, wherein the composition is administered orally or parenterally.

25. A liquid composition comprising warfarin sodium as an active ingredient, glycerin in an amount of about 20 to 93% of the composition by volume to act as a stabilizer and water, wherein the liquid composition has a pH above 5 and the amount of warfarin sodium in the composition that is degraded after at least 1 month at room temperature is about 5% or less.

26. A method for preparing the stable liquid composition of claim 25, which comprises providing the amount of glycerin in the composition to act as a stabilizer and providing the composition with the pH above 5.

* * * * *